United States Patent [19]

Grollier et al.

[11] Patent Number: 5,053,410

[45] Date of Patent: Oct. 1, 1991

[54] COMBINATION OF DERIVATIVES OF PYRIMIDINE AND OF NONSTEROID ANTIINFLAMMATORY AGENTS FOR INDUCING AND STIMULATING THE GROWTH OF HAIR AND REDUCING ITS LOSS

[75] Inventors: Jean F. Grollier, Paris; Georges Rosenbaum, Asnières, both of France

[73] Assignee: L'Oreal, Paris, France

[21] Appl. No.: 288,381

[22] Filed: Dec. 22, 1988

[30] Foreign Application Priority Data

Dec. 22, 1987 [LU] Luxembourg ............................ 87090

[51] Int. Cl.$^5$ ........................ A61K 7/06; A61K 9/12; A61K 31/505
[52] U.S. Cl. ...................................... 514/256; 424/47; 424/70; 514/570; 514/880; 514/881; 514/937; 514/938; 514/944
[58] Field of Search ................ 514/570, 256, 171, 880

[56] References Cited

U.S. PATENT DOCUMENTS

| | | | |
|---|---|---|---|
| 4,141,976 | 2/1979 | Voorhees | 424/240 |
| 4,579,844 | 4/1986 | Rovee et al. | 514/171 |
| 4,596,812 | 6/1986 | Chidsey | 514/256 |
| 4,684,635 | 8/1987 | Orentreich et al. | 514/171 |

FOREIGN PATENT DOCUMENTS

| | | | |
|---|---|---|---|
| 0220118 | 4/1987 | European Pat. Off. | 424/70 |
| 61-260010 | 11/1986 | Japan | 514/256 |

OTHER PUBLICATIONS

Chemical Abstracts, vol. 106, No. 24, No. 201544m.
Patent Abstracts of Japan, vol. 11, No. 115 (C-415) [2562], Apr. 10, 1987.
Merck Index, 9th edition, 1976, pp. 407 and 535.

*Primary Examiner*—Dale R. Ore
*Attorney, Agent, or Firm*—Fleit, Jacobson, Cohn, Price, Holman & Stern

[57] ABSTRACT

The invention relates to the combination of derivatives of pyrimidine and of nonsteroid antiinflammatory agents with a view to inducing and stimulating the growth of hair and reducing its loss.

20 Claims, No Drawings

COMBINATION OF DERIVATIVES OF PYRIMIDINE AND OF NONSTEROID ANTIINFLAMMATORY AGENTS FOR INDUCING AND STIMULATING THE GROWTH OF HAIR AND REDUCING ITS LOSS

The invention relates to the combination of derivatives of pyrimidine and of nonsteroid antiinflammatory agents with a view to inducing and stimulating the growth of hair and reducing its loss.

The activity of hair follicles is cyclic. The active anagen phase, which lasts several years and during which the hair lengthens, is followed by a phase of rest (telogen) of a few months. After this period of rest the hair falls out and another cycle begins again.

The head of hair is thus continually renewed; out of the 100,000 to 150,000 hairs which make up a head of hair, at any time approximately 10% are at rest and will therefore be replaced in a few months.

In almost all cases, the loss of hair appears in individuals who are genetically susceptible; more particularly, it affects men.

This alopecia is a disorder of the renewal of hair which, in a first stage, entails an acceleration of the cycle frequency at the expense of the quality of hair, and then of its quantity. There is a progressive depletion of hair due to regression of a part of so-called "terminal" hair at the "down" stage. Regions are affected preferentially: temporal-frontal bays in men; diffuse alopecia of the crown in women.

In certain dermatoses of the scalp of an inflammatory nature such as, for example, psoriasis or seborrhoeic dermatitis, hair loss may be greatly accentuated or may entail strongly perturbed follicular cycles.

Compounds such as 6-amino-1,2-dihydro-1-hydroxy-2-imino-4-piperidinopyrimidine or minoxidil have already been proposed in the past for use in compositions making it possible to reduce or to eliminate the effect of alopecia and to induce or to stimulate the growth of hair and to reduce its loss.

The Applicant has now found that combining certain nonsteroid antiinflammatory agents with certain pyrimidine derivatives and, more particularly, minoxidil resulted surprisingly in the finding of an improved action and stimulation of the growth of hair and a more powerful action on the retardation of hair loss. This is particularly surprising when it is known that nonsteroid antiinflammatory agents do not, a priori, affect the pilary cycle in any way.

The Applicant found, in particular, that the combination was having a superior activity when compared with the pyrimidine derivatives employed by themselves and that this action was also quicker by virtue of the use of the combination.

This combination makes it possible, in particular, to employ the pyrimidine derivatives at a lower concentration.

The Applicant found that certain nonsteroid antiinflammatory agents were particularly suitable for use in combination with minoxidil or its derivatives in topical application, especially with a view to a long-term treatment. The compounds of interest have particularly low toxicity, have improved storage characteristics in combination with minoxidil, especially in an anhydrous medium, and furthermore have a cosolubilizing effect on pyrimidine derivatives such as minoxidil, especially in an anhydrous medium.

In order to determine the effectiveness or the speed of action of a composition for treating alopecia, use is generally made of the trichogram, and more particularly the phototrichogram, which makes it possible to determine, inter alia, the percentage of hair in an anagen phase, relative to hair in a telogen phase.

A subject of the invention consists, therefore, of the combination of pyrimidine derivatives with nonsteroid antiinflammatory agents with a view to inducing or stimulating the growth of hair and reducing its loss.

Another subject of the invention consists of cosmetic or pharmaceutical compositions containing such a combination.

A further subject of the invention is devices with a number of compartments, also known as "kits" or treatment packs incorporating the various components of the combination.

Other subjects of the invention will become apparent on reading the description and the examples which follow.

The combination in accordance with the invention is essentially characterized in that it comprises:

a) a component (A) containing, in a physiologically acceptable medium, at least one nonsteroid antiinflammatory agent chosen from the oxicams, niflumic acid, diclofenac, diflunisal, flufenamic acid, bufexamac, fenbufen and fenoprofen, b) a component (B) containing, in a physiologically acceptable medium, at least one pyrimidine derivative corresponding to the formula:

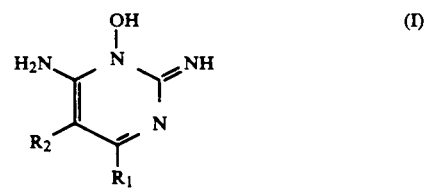

(I)

in which $R_1$ denotes a group

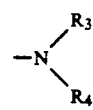

$R_3$ and $R_4$, independently of each other, denoting hydrogen or an alkyl, alkenyl, alkylaryl or cycloalkyl group; $R_3$ and $R_4$ being also able to form a heterocyclic ring with the nitrogen atom to which they are linked, which is chosen from aziridinyl, azetidinyl, pyrrolidinyl, piperidyl, hexahydroazepinyl, heptamethyleneimine, octamethyleneimine, morpholine and 4-(lower)alkylpiperazidinyl groups, it being possible for the heterocyclic groups to be substituted on the carbon atoms by one to three lower alkyl, hydroxyl or alkoxy groups; the group $R_2$ is chosen from a hydrogen atom and an alkyl, alkenyl, alkylalkoxy, cycloalkyl, aryl, alkylaryl, arylalkyl, alkylarylalkyl, alkoxyarylalkyl or haloarylalkyl group, and the addition salts of physiologically acceptable acids, the components (A) and (B) forming part of the same single composition or being intended to be employed separately, either simultaneously or successively or after an interval of time with a view to inducing and stimulating the growth of hair and reducing its loss.

Among the oxicams, piroxicam may be mentioned in particular.

In the compounds of formula (I), the alkyl or alkoxy groups preferably denote a group containing 1 to 4 carbon atoms; the alkenyl group preferably denotes a group containing 2 to 5 carbon atoms; the aryl group preferably denotes phenyl, and the cycloalkyl group preferably denotes a group containing 4 to 6 carbon atoms.

The compounds of formula (I) which are preferred are chosen more particularly from the compounds in which $R_2$ denotes hydrogen, and $R_1$ denotes a group:

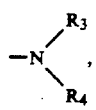

in which $R_3$ and $R_4$ form a piperidyl ring, and their salts such as, for example, the sulphate.

A particularly preferred compound among these compounds consists of 6-amino-1,2-dihydro-1-hydroxy-2-imino-4-piperidinopyrimidine, also known as minoxidil.

The antiinflammatory agent which is particularly preferred is niflumic acid.

The nonsteroid antiinflammatory agents defined above are employed in component (A) in proportions of between 0.01 and 5% by weight, preferably between 0.05 and 3% by weight, and more particularly between 0.05 and 2% by weight; the pyrimidine derivative of formula (I) is employed in component (B) in proportions of between 0.05 and 10% by weight, preferably between 0.05 and 5% by weight and in particular between 0.5 and 4% by weight.

When the components (A) and (B) are employed in the same single composition, the nonsteroid antiinflammatory agent defined above is employed in proportions of between 0.01 and 3% by weight relative to the total weight of the composition, preferably between 0.02 and 2% and in particular between 0.02 and 1%.

In this case the pyrimidine derivative of formula (I) is employed in the compositions in a proportion of between 0.05 and 6% by weight relative to the total weight of the composition, preferably between 0.1 and 5% by weight and in particular between 0.5 and 3% by weight.

The physiologically acceptable medium employed for the components (A) and (B) is a medium which may be employed in cosmetic formulation and may consist of water or a mixture of water and of one or more solvents or of one or more solvents. The solvents are pharmaceutically or cosmetically acceptable organic solvents.

The medium which is particularly preferred is an anhydrous medium, that is to say containing less than 1% of water.

The solvents which are particularly preferred are chosen from $C_1$–$C_4$ lower alcohols such as ethyl alcohol, isopropyl alcohol, tert-butyl alcohol, alkylene glycols such as propylene glycol, mono- and dialkylene glycol alkyl ethers in which the alkyl and alkylene groups preferably contain 1 to 4 carbon atoms, such as more particularly ethylene glycol monoethyl ether, propylene glycol monomethyl ether and diethylene glycol monoethyl ether.

The anhydrous medium preferably consists of a $C_1$–$C_4$ lower alcohol or a mixture of $C_1$–$C_4$ alcohol with an alkylene glycol.

The physiologically acceptable media may be thickened or not, and thickening or gelling agents which are well known in the state of the art may be employed for thickening, such as, more particularly, heterobiopolysaccharides like xanthan gum or scleroglucans, cellulose derivatives, and crosslinked or uncrosslinked acrylic polymers.

When they are employed in an aqueous medium, the solvents are preferably present in proportions of between 1 and 80% by weight relative to the total weight of the composition or of each of the components.

The thickeners are preferably employed in proportions of between 0.1 and 5% by weight and in particular between 0.4 and 3% by weight relative to the total weight of each of the components when they are employed separately or relative to the total weight of the composition containing the components (A) and (B).

The compositions consisting either of the components (A) and (B) or of the composition containing both components (A) and (B) may also contain any other adjuvants which are usually employed in compositions intended for a topical application for cosmetic or pharmaceutical use, and more particularly preserving agents, complexing agents, colorants, alkalifying or acidifying agents, anionic, cationic, nonionic or amphoteric surface-active agents or mixtures thereof, and anionic, cationic, nonionic or amphoteric polymers, as well as mixtures thereof.

The pH of these compositions may vary between 4 and 9.

These compositions may also be packaged under pressure in aerosol devices in the presence of a propellant.

In component (B), the pyrimidine derivatives of formula (I) may be present either in dissolved form in the physiologically acceptable media or else totally or partially suspended in this medium, and more particularly in the form of particles which have a particle size of less than 80 microns, preferably less than 20 microns and in particular less than 5 microns.

An embodiment of the invention consists in employing the combination in accordance with the invention in the form of a single composition containing the components (A) and (B).

A particularly preferred form of the invention consists in storing the components (A) and (B) in separate devices and preparing the composition containing these two components just before application.

Lastly, another embodiment consists in applying the components (A) and (B) separately, either simultaneously or successively or after an interval of time. In this embodiment, composition (A), is preferably applied before composition (B).

In this case, the combination in accordance with the invention may be packaged, in particular, in a multicompartment device known as a kit or outfit, in which a first compartment contains the component (A) including the nonsteroid antiinflammatory agent defined above, and the second compartment contains the component (B) based on the pyrimidine derivative of formula (I).

These compositions are preferably applied to the hair or to the scalp. For example, they may be applied after the scalp and the hair have been washed with a shampoo.

A preferred embodiment consists in applying 1 to 2 grams of the composition according to the invention to the alopecic region at a frequency of one to two applications a day for 1 to 7 days a week, this being done for a period of 1 to 6 months.

In accordance with the invention, the composition containing the nonsteroid antiinflammatory agent may also be applied in the evening and the component (B) in the morning.

The preferred embodiment consists in applying the components (A) and (B) in succession or even simultaneously by making a mixture at the time of the application.

For this purpose, the multicompartment devices may be equipped with a mixing device, well known in the state of the art.

The process in accordance with the invention is aimed at the therapeutic treatment of hair loss, insofar as it affects the dysfunction of the biological mechanisms at the source of the growth of hair.

Another subject of the invention is therefore a process for the preparation of a medication optionally containing two components and intended for treating the loss of hair and in particular alopecia.

This process may also be considered as a process of cosmetic treatment of hair, insofar as it improves its appearance.

The following examples are intended to illustrate the invention without, however, being limiting in nature.

EXAMPLE 1

Two compositions (A) and (B) are packaged as a kit containing, respectively:

| Composition (A): | |
|---|---|
| Piroxicam | 0.20 g |
| Propylene glycol | 20.00 g |
| Ethyl alcohol | 50.00 g |
| Water q.s. | 100.00 g |
| Composition (B): | |
| Minoxidil | 1.50 g |
| Propylene glycol | 20.00 g |
| Ethyl alcohol | 50.00 g |
| Water q.s. | 100.00 g |

The extemporaneous mixture of both compositions (A) and (B) is applied to the alopecic parts of the scalp.

EXAMPLE 2

Two compositions (A) and (B) are packaged as a kit containing, respectively:

| Composition (A): | |
|---|---|
| Diflunisal | 0.50 g |
| Propylene glycol | 20.00 g |
| Ethyl alcohol | 50.00 g |
| Water q.s. | 100.00 g |
| Composition (B): | |
| Minoxidil | 1.80 g |
| Ethyl alcohol | 95.00 g |
| Propylene glycol q.s. | 100.00 g |

The compositions (A) and (B) are applied in succession after an interval of time to the alopecic parts of the scalp. Composition (A) is applied in the morning and composition (B) in the evening.

EXAMPLE 3

The following composition is prepared:

| Diclofenac | 0.08 g |
|---|---|
| Minoxidil | 1.40 g |
| Ethyl alcohol | 50.00 g |
| Propylene glycol | 20.00 g |
| Xanthan gum sold by Kelco under the name "Keltrol T" | 0.80 g |
| Water q.s. | 100.00 g |

This composition is applied as shown in Example 2.

EXAMPLE 4

Two compositions (A) and (B) are packaged as a kit containing, respectively:

| Composition (A): | |
|---|---|
| Flufenamic acid | 0.15 g |
| Propylene glycol | 20.00 g |
| Ethyl alcohol | 50.00 g |
| Water q.s. | 100.00 g |
| Composition (B): | |
| Minoxidil | 2.50 g |
| Propylene glycol | 20.00 g |
| Ethyl alcohol | 50.00 g |
| Hydroxypropyl cellulose sold by Hercules under the name "Klucel G" | 2.00 g |
| Water q.s. | 100.00 g |

The two compositions (A) and (B) are applied to the alopecic parts of the scalp in succession after an interval of time: composition (A) in the morning and composition (B) in the evening.

EXAMPLE 5

Two compositions (A) and (B) are packaged as a kit containing, respectively:

| Composition (A): | |
|---|---|
| Niflumic acid | 0.30 g |
| Propylene glycol | 20.00 g |
| Ethyl alcohol | 50.00 g |
| Xanthan gum sold by Kelco under the name "Keltrol T" | 0.70 g |
| Water q.s. | 100.00 g |
| Composition (B): | |
| Minoxidil | 2.00 g |
| Propylene glycol | 20.00 g |
| Ethyl alcohol | 50.00 g |
| Xanthan gum sold by Kelco under the name "Keltrol T" | 0.70 g |
| Water q.s. | 100.00 g |

The compositions (A) and (B) are applied in succession after an interval of time to the alopecic parts of the scalp on alternate days: first day application of composition (A), second day application of composition (B).

EXAMPLE 6

The following composition is prepared:

| Niflumic acid | 3.75 g |
|---|---|
| Minoxidil | 0.625 g |
| Distilled propylene glycol | 6.45 g |

| | |
|---|---|
| -continued | |
| Absolute ethyl alcohol q.s. | 100.00 g |

This lotion, applied daily to the alopecic regions of the scalp, produces a positive effect on fresh growth of hair and a decrease in its loss.

EXAMPLE 7

| | |
|---|---|
| Bufoxamac | 3.00 g |
| Minoxidil | 1.00 g |
| Distilled propylene glycol | 6.45 g |
| Absolute ethyl alcohol q.s. | 100.00 g |

EXAMPLE 8

Two compositions (A) and (B) are packaged as a kit containing, respectively:

| | |
|---|---|
| Composition (A): | |
| Flufenamic acid | 5.00 g |
| Distilled propylene glycol | 6.45 g |
| Absolute ethyl alcohol q.s. | 100.00 g |
| Composition (B): | |
| Minoxidil | 1.00 g |
| Distilled propylene glycol | 6.45 g |
| Absolute ethyl alcohol q.s. | 100.00 g | whereof equal weights (50/50) of the said compositions are mixed before the application.

EXAMPLE 9

The following composition is prepared:

| | |
|---|---|
| Diflunisal | 4.00 g |
| Minoxidil | 0.8 g |
| Distilled propylene glycol | 6.45 g |
| Absolute ethyl alcohol q.s. | 100.00 g |

EXAMPLE 10

Two compositions (A) and (B) are packaged as a kit containing, respectively:

| | |
|---|---|
| Composition (A): | |
| Diclofenac | 1.4 g |
| Distilled propylene glycol | 6.45 g |
| Absolute ethyl alcohol q.s. | 100.00 g |
| Composition (B): | |
| Minoxidil | 1.00 g |
| Distilled propylene glycol | 6.45 g |
| Absolute ethyl alcohol q.s. | 100.00 g |

These compositions are applied after an interval of time, one in the morning (A), the other in the evening (B).

EXAMPLE 11

Two compositions (A) and (B) are packaged as a kit containing, respectively:

| | |
|---|---|
| Composition (A): | |
| Fenbufen | 3.00 g |
| Distilled propylene glycol | 6.45 g |
| Absolute ethyl alcohol q.s. | 100.00 g |
| Composition (B): | |

| | |
|---|---|
| -continued | |
| Minoxidil | 0.70 g |
| Distilled propylene glycol | 6.45 g |
| Absolute ethyl alcohol q.s. | 100.00 g |

(A) and then (B), or vice versa, are applied in immediate succession to the alopecic regions of the scalp.

EXAMPLE 12

Two compositions (A) and (B) are packaged as a kit containing, respectively:

| | |
|---|---|
| Composition (A): | |
| Fenoprofen | 2.5 g |
| Distilled propylene glycol | 6.45 g |
| Absolute ethyl alcohol q.s. | 100.00 g |
| Composition (B): | |
| Minoxidil | 1.50 g |
| Distilled propylene glycol | 6.45 g |
| Absolute ethyl alcohol q.s. | 100.00 g |

The compositions (A) and (B) are applied, alternating daily.

EXAMPLE 13

Two compositions (A) and (B) are packaged as a kit containing, respectively:

| | |
|---|---|
| Composition (A): | |
| Piroxicam | 0.4 g |
| Propylene glycol monomethyl ether | 75.0 g |
| Absolute ethyl alcohol q.s. | 100.00 g |
| Composition (B): | |
| Minoxidil | 2.50 g |
| Distilled propylene glycol | 6.45 g |
| Absolute ethyl alcohol | 100.00 g |

These compositions are applied to the alopecic regions of the scalp in succession after an interval of time, one in the morning (A), the other in the evening (B) or vice versa.

We claim:

1. A combination of components that is effective for use in inducing and stimulating hair growth and for decreasing hair loss or for improving the appearance of the hair, said combination comprising:
   (a) a first component (A), comprising a physiologically acceptable medium and an effective amount of least one nonsteroid anti-inflammatory agent selected from the group consisting of the oxicams, niflumic acid, diclofenac, diflunisal, flufenamic acid, bufexamac, fenbufen, fenoprofen and physiologically acceptable salts or esters of the oxicams, niflumic acid, diclofenac, diflunisal, flufenamic acid, bufexamac, fenbufen, or fenoprofen; and
   (b) a second component (B), comprising a physiologically acceptable medium and an effective amount of at least one pyrimidine derivative having the formula:

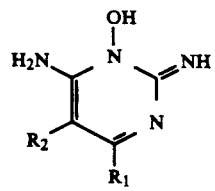

as well as acid addition salts thereof, wherein $R_1$ represents a group having the formula:

wherein $R_3$ and $R_4$ are selected from the group consisting of hydrogen, lower alkyl, alkenyl, alkylaryl and cycloalkyl, the alkyl part of which is a lower alkyl radical, or $R_3$ and $R_4$, with the nitrogen to which they are each bound, form a heterocyclic group, which is unsubstituted or is substituted on the carbon atoms with one to three lower alkyl, hydroxy, or alkoxy, and which is selected from the group consisting of aziridinyl, azetidinyl, pyrrolidinyl, piperidino, hexahydrolazepinyl, heptamethylenimino, octamethyleneimino, morpholino and 4-(lower alkyl)piperazinyl, and wherein $R_2$ is selected from the group consisting of hydrogen, lower alkyl, alkenyl, alkoxyalkyl, cycloalkyl, aryl, alkylaryl, arylalkyl, alkylarylalkyl, alkoxyarylalkyl and haloarylalkyl, the alkyl part of which is a lower alkyl radical, wherein said components are used as separate components that are used either successively or intermittently or are mixed immediately prior to use for use as a composition containing said components and wherein said effective amount of each component is effective, when used as a combination, to induce and stimulate hair growth and reduce its loss.

2. The combination of claim 1, wherein said oxicam is piroxicam.

3. The combination of claim 1, wherein said compound of formula (I) is 6-amino-1,2-dihydro-1-hydroxy-2-imino-4-piperidinopyrimidine or minoxidil.

4. The combination of claim 1, wherein said nonsteroid anti-inflammatory agent is at a concentration of between 0.01 and 5% by weight of component (A) and said amount of said pyrimidine derivative of formula (I) is at a concentration of between 0.05 and 10% by weight of component (B).

5. The combination of claim 4, wherein the concentration of said nonsteroid anti-inflammatory agent is between 0.05 and 3% by weight.

6. The combination of claim 4, wherein the concentration of said nonsteroid anti-inflammatory agent is between 0.05 and 2% by weight.

7. The combination of claim 4, wherein the concentration of said pyrimidine derivative is between 0.05 and 5% by weight.

8. The combination of claim 4, wherein the concentration of said pyrimidine derivative is between 0.05 and 4% by weight.

9. The combination of claim 1, wherein said components (A) and (B) are used as a composition and the concentration of said nonsteroid anti-inflammatory agent is between 0.01 and 3% by weight relative to the total weight of the composition and the concentration of said pyrimidine derivative of formula (I) is between 0.05 and 6% by weight relative to the total weight of the composition.

10. The combination of claim 5, wherein the concentration of said nonsteroid anti-inflammatory agent in said composition is between 0.02 and 2% by weight.

11. The combination of claim 5, wherein the concentration of said nonsteroid anti-inflammatory agent in said composition is between 0.02 and 1% by weight.

12. The combination of claim 5, wherein the concentration of said pyrimidine derivative in said composition is between 0.1 and 5% by weight.

13. The combination of claim 5, wherein the concentration of said pyrimidine derivative in said composition is between 0.5 and 3% by weight.

14. The combination of claim 1, wherein said physiologically acceptable medium is selected from the group consisting of water, a mixture of water and one or more organic solvents, and one or more cosmetically or pharmaceutically acceptable organic solvents.

15. The combination of claim 1, wherein said physiologically acceptable medium is anhydrous and contains cosmetically or pharmaceutically acceptable organic solvents.

16. The combination of claim 14, wherein said solvents are selected from the group consisting of $C_1$–$C_4$ lower alcohols, alkylene glycols and mono-and dialkylene glycol alkyl ethers.

17. The combination of claim 1, wherein at least one physiologically acceptable medium of the components (A) and (B) is thickened by means of thickening agents, gelling agents, or both thickening and gelling agents.

18. The combination of claim 1, wherein at least one of the components (A) and (B) also contains at least one cosmetically or pharmaceutically acceptable adjuvant selected from the group consisting of preserving agents, complexing agents, colorants, alkalifying agents, acidifying agents, anionic surface-active agents, nonionic surface-active agents, amphoteric surface-active agents, mixtures of anionic surface-active agents, nonionic surface-active agents, and amphoteric surface-active agents, anionic polymers, cationic polymers, amphoteric polymers and mixtures of anionic polymers, cationic polymers and amphoteric polymers.

19. A process for the cosmetic treatment of the hair or of the scalp, comprising applying the combination of claim 1 to the hair or to the scalp.

20. A multicompartment device or kit, comprising at least two compartments wherein one of said compartments contains component (A) of the combination of claim 1 and another of said compartments contains component (B) of the combination of claim 15.

* * * * *